US009841429B2

(12) United States Patent
Livache et al.

(10) Patent No.: US 9,841,429 B2
(45) Date of Patent: Dec. 12, 2017

(54) METHOD FOR REAL-TIME MEASUREMENT OF THE INDIVIDUAL SECRETIONS OF A CELL

(71) Applicants: Thierry Livache, Jarrie (FR); Yoann Roupioz, Theys (FR); Sarah Milgram, Moretel des Mailles (FR); Bernard Maillere, Versailles (FR); Patrice Marche, Meylan (FR)

(72) Inventors: Thierry Livache, Jarrie (FR); Yoann Roupioz, Theys (FR); Sarah Milgram, Moretel des Mailles (FR); Bernard Maillere, Versailles (FR); Patrice Marche, Meylan (FR)

(73) Assignees: COMMISSARIANT A L'ENERGIE ATOMIQUE ET AUX ENERGIES ALTERNATIVES, Paris (FR); INSTITUT NATIONAL DE LA SANTE ET DE LA RECHERCHE MEDICALE, Paris (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 0 days.

(21) Appl. No.: 13/690,779

(22) Filed: Nov. 30, 2012

(65) Prior Publication Data
US 2013/0137085 A1    May 30, 2013

(30) Foreign Application Priority Data
Nov. 30, 2011   (FR) ..................................... 11 60964

(51) Int. Cl.
G01N 33/543    (2006.01)
G01N 33/68    (2006.01)
(Continued)

(52) U.S. Cl.
CPC ....... *G01N 33/6866* (2013.01); *G01N 21/553* (2013.01); *G01N 33/5038* (2013.01);
(Continued)

(58) Field of Classification Search
CPC .......... G01N 33/5011; G01N 2800/52; G01N 33/6893; G01N 2500/00; G01N 2500/04;
(Continued)

(56) References Cited

U.S. PATENT DOCUMENTS

2009/0093013 A1*   4/2009   Fang .................... G01N 21/211
                                                  435/29
2011/0111981 A1*   5/2011   Love et al. ..................... 506/10

OTHER PUBLICATIONS

Zhu et al. ("A microdevice for multiplexed detection of T-cell-secreted cytokines", Lab Chip. 8, 2197-2205 (2008), doi:10.1039/b810244a).*

(Continued)

*Primary Examiner* — Melanie Y Brown
*Assistant Examiner* — Richard Moerschell
(74) *Attorney, Agent, or Firm* — Hunton & Williams LLP

(57) ABSTRACT

The present invention relates to a method for real-time measurement of the secretion of at least one compound by at least one individual cell, comprising:
  the culturing, in a liquid medium, of at least one cell in a culture chamber, at least one wall of which comprises at least one sensitive area, a sensitive area comprising a plurality of ligands, attached to a solid support, each ligand being able to bind specifically to the compound, and an element for real-time transduction of a signal produced by the binding of the compound to one of the ligands;
  the identification, in a sensitive area, of at least one spot producing a signal;
(Continued)

the real-time measurement of the signal produced by the spot identified, representing the amount of compound secreted by an individual cell.

19 Claims, 3 Drawing Sheets

(51) Int. Cl.
G01N 33/50 (2006.01)
G01N 21/552 (2014.01)
B01L 3/00 (2006.01)

(52) U.S. Cl.
CPC ... *G01N 33/5044* (2013.01); *G01N 33/54373* (2013.01); *B01L 3/5085* (2013.01)

(58) Field of Classification Search
CPC ... G01N 33/57484; G01N 2333/91215; G01N 2333/475; G01N 2333/525; G01N 33/5023; G01N 21/553; G01N 21/554; G01N 2500/10
See application file for complete search history.

(56) References Cited

OTHER PUBLICATIONS

Revzin et al. ("Biosensors for immune cell analysis—A perspective", Biomicrofluidics, vol. 6, No. 2, Jan. 1, 2012 (Jan. 1, 2012), pp. 021301-1-021301-1, XP055049362, DOI: 10.1063/1.4706845).*

Hide et al. ("Real-Time Analysis of Ligand-Induced Cell Surface and Intracellular Reactions of Living Mast Cells Using a Surface Plasmon Resonance-Based Biosensor" Analytical Biochemistry, 302, 28-37 (2002) ).*

Milgram et al. ("On chip real time monitoring of B-cells hybridoma secretion of immunoglobulin", Biosensors and Bioelectronics, vol. 26, Issue 5, Jan. 15, 2011, Available online Sep. 29, 2010, pp. 2728-2732).*

Peterson et al. ("Surface plasmon resonance imaging of cells and surface-associated fibronectin" BMC Cell Biology, 10:16 (2009)).*

Scarano et al. ("Surface plasmon resonance imaging for affinity-based biosensors" Biosensors & Bioelectronics, 25 (5) (2010), pp. 957-966).*

Shirasaki et al. ("Single Cell Real Time Secretion Assay Using Amorphous Fluoropolymer Microwell Array" IEEE, M4C.002, 978-1-4577-0156-6111, Jun. 5, 2011).*

Stybayeva et al. ("Detecting interferon-gamma release from human CD4 T-cells using surface plasmon resonance" Colloids and Surfaces, 80 (2) (2010), pp. 251-255).*

Thillaivinayagalingam et al. ("Biopharmaceutical production: Applications of surface plasmon resonance biosensors" Journal of Chromatography B, vol. 878, Issue 2, Jan. 15, 2010, pp. 149-153, Immunoaffinity Techniques in Analysis).*

Shirasaki et al. ("Single cell real time secretion assay using amorphous fluoropolymer microwell array" M4C.002, IEEE, Transducers '11 , Beijing, China, Jun. 5-9, 2011).*

Zhu et al. ("A miniature cytometry platform for capture and characterization of T-lymphocytes from human blood" analytica chimica acta 608, 2008, 186-196).*

Czerkinsky et al., Journal of Immunological Methods, 65:109-121 (1983).

Arvilommi et al., APMIS, 104:401-410 (1996).

Wang et al., Nat Chem., doi:10.1038/nchem.961 (2011).

Peterson et al., BMC Cell Biology, doi:10.1186/1471-2121-10-16 (2009).

Yanase et al., Biosensors and Bioelectronics, 26: 674-681 (2010).

* cited by examiner

METHOD FOR REAL-TIME MEASUREMENT OF THE INDIVIDUAL SECRETIONS OF A CELL

CROSS-REFERENCE TO RELATED APPLICATIONS

This is a Utility filing of a French Application Filing FR 1160964, filed Nov. 30, 2011, the disclosure of which is hereby incorporated by reference in its entirety.

FIELD OF THE INVENTION

The present invention relates to a method for the real-time determination and quantification of compounds secreted by an individual cell.

TECHNICAL BACKGROUND

Communication between cells is a biological event of primary importance. It can take place in order to enable a signal to be transferred between single-cell entities, but also and especially between the cells of the same organism. The modes of communication can have various forms, such as a physical contact between cells or else the emission of compounds by one cell and the reception of these compounds by another cell. In the latter mode, which is a mode of chemical communication, it is a set of parameters, including the nature, the amount, the frequency and the duration of secretion of the compounds, which carries the information, and also the cell type of the cell emitting the message and the cell type of the message recipient cell (or "target" cell).

Thus, the complex network of secretory activities is the subject of numerous biomedical investigations: this involves all the immune cascades, of which, on the one hand, normal operation is involved in certain diseases, for example infections, cancers, and of which, on the other hand, dysfunctions can result in pathological states, such as an autoimmune disease or an allergy. Moreover, the manipulation of the immune cascades is of interest for preventing certain pathological states, as is the case for vaccines or the treatment of transplant rejections. The possibility of monitoring the triggering of an immune response is therefore an important issue for many diagnostic and therapeutic biomedical applications.

In this context, it is important to be able to detect the cell secretions on the scale of a single cell in order to differentiate the various cell populations concerned.

At the current time, a single product which allows the analysis of the immune response on the cellular scale is approved for diagnostic use. It is the T-SPOT®. TB (Oxford Immunotec) diagnostic test for tuberculosis, in particular described in international application WO 98/23960 and in the article by Leung et al. (2010) *American Journal of Respiratory and Critical Care Medicine* 182:834-840. This test is based on the "ELISPOT" technique developed in the 1980s (Czerkinsky et al. (1983) *J. Immunol. Methods* 65:109-21). This technique involves culturing, in multi-well plates, cell samples for more or less long periods of time (from a few hours to a few days), followed by washing of these wells (removal of the secretory cells) and by a succession of washing/visualizing steps according to the principle of the ELISA sandwich assay: since the bottom of these wells is coated with antibodies specific for a secreted compound, a molecular assembly using a second antibody followed by colorimetric visualization makes it possible to visualize, a posteriori, spots in the place where a cell has sedimented during the culture and secreted a compound into the culture medium. The diffusion of the compounds into the surroundings close to a cell thus makes it possible to reveal spots characteristic of an individual cell secretory activity.

However, although it is increasingly used, this approach suffers from various limits, including a relatively long incubation time (from one to two days) before the visualization step, and also the impossibility of collecting the samples containing secretory cells since the latter are lyzed before carrying out the labeling step. Finally, it should be specified that the ELISPOT technique does not make it possible to provide access to the kinetic parameters of cell secretion.

Various techniques which make it possible to have access to cell secretions in real time are known.

It is thus possible to mention the patch-clamp method in which it is possible to quantify, by measurement of capacitance and/or amperometric measurement, the secretion of electrically charged compounds by the part of the plasma membrane blocking the pipette (see, for example, Westerink & Ewing (2008) *Acta Physiol.* (Oxf) 192:273-85). However, this method has several drawbacks. First of all, it requires isolating a cell. Next, it does not make it possible to have access to the secretions of a cell as a whole. Finally, it only makes it possible to measure the secretion of electrically charged compounds, and furthermore in a nonspecific manner.

Other techniques involve the real-time chemical or enzymatic visualization of secreted compounds. In these techniques, this involves adding to the cell culture medium one or more reagent(s) capable of reacting with the product secreted by cells. This may be, for example, luminol which reacts with the reactive oxygen species that are produced by monocytes during their differentiation into macrophages (Kasai et al. (2005) *Analytica Chimica Acta* 549:14-19) or enzymes which metabolize the products released (Clark et al. (2009) *Analytical Chemistry* 81:2350-2356; Inoue et al. (2010) *Biosens Bioelectron.* 25:1723-8). However, in addition to requiring the addition of elements not essential to the cell culture, these approaches are limited to the study of secreted compounds which must either have particular chemical properties or be enzymatic substrates (such as glycerol, for example) in order to be detected. In fact, this technique excludes virtually all the proteins that can be found in a biological sample, which might explain the lack of an example of application of this technique to the detection of cytokines.

Finally, it has recently been shown that optical techniques, in particular surface plasmon resonance imaging (SPRi), can be successfully used for detecting cell secretions, but without making it possible to measure a specific secretion on an individual-cell scale.

Thus, Stybayeva et al. (2010) *Colloids Surf B. Biointerfaces* 80:251-5 describe an analysis using two modules, or compartments: one dedicated to the specific capture of cell types of interest, and the other to the analysis of the conditioned extracellular medium. However, this assembly does not make it possible to establish a link between a secreted product and a particular secretory cell.

Moreover, Peterson et al. (2009) *BMC Cell. Biol.* 10:16 describe a method demonstrating the secretion, on a cellular scale, of biomolecules into the extracellular medium, but not making it possible to identify the nature of the products secreted.

Finally, Milgram et al. (2011) *Biosens. Bioelectron.* 26:2728-2732 and Milgram et al. (2009) *IEEE Sensors Journal* 1768-1771, describe a method enabling the real-time evaluation of the presence of an analyte in a solution. The main advantage of the Milgram et al. method is the real-time detection of the analyte in solution, which is not possible using ELISA. However, this method does not give access to the individual secretions of a cell.

DESCRIPTION OF THE INVENTION

The present invention ensues from the unexpected demonstration, by the inventors, that it was possible to specifically monitor, in real time, the secretion of a compound by an individual cell by surface plasmon resonance imaging.

Thus, the present invention relates to a method for real-time measurement of the secretion of at least one compound by at least one individual cell, comprising:
- the culturing of at least one cell in a culture chamber, at least one wall of which comprises at least one sensitive area, a sensitive area comprising at least one ligand, attached to a solid support, the ligand being able to bind specifically to a compound, and an element for real-time measurement of a signal produced by the binding of a compound to the ligand;
- the identification, in a sensitive area, of at least one spot emitting a signal produced by the binding of at least one compound respectively to at least one ligand;
- the real-time measurement of the signal produced by the spot identified, representing the amount of compound secreted by an individual cell.

As it is understood here, the "signal" is produced during and/or from the binding of the compound to the ligand and can be measured by the signal measurement element. The "measurement" of a signal denotes the determination of the presence or absence of the signal, and/or the quantification thereof. The expression "real time" means that the signal is produced and measured essentially at the moment the binding of the compound and of the ligand takes place.

The measurement of the signal according to the invention is carried out directly. Thus, the signal does not need to be mediated by molecules present in the culture chamber or added to the culture chamber, other than the compound and the ligand, in order to be produced. By way of example, the signal according to the invention does not come from an oxidoreduction probe, or from the additional binding of a label specific for the compound, such as a labeled antibody, to a compound already bound by the ligand. The measurement of the signal according to the invention can be carried out by an element such as an optical reading system, for instance a surface plasmon resonance imager.

The signal can be measured using an optical technique sensitive to interactions taking place on a support, and preferably by surface plasmon resonance. The surface plasmon resonance optical reading systems are well known to those skilled in the art and generally combine a light source, for example of LED type, in order to cause a plasmon excitation, and a camera, for example of CCD type, to record the signal produced by the plasmon resonance. In this respect, it is preferable for the signal to be monitored in imaging mode, rather than in single-point reading mode, in particular in order to monitor in real time the disruptions associated with cell events. As those skilled in the art well know, the imaging mode consists in monitoring the variations in signal of all the pixels constituting the image of the CCD camera used, whereas the single-point mode itself consists in defining or in predefining, regions of the image, i.e. a set of pixels, of which the average of the signals obtained reflects an average signal for the region of the image chosen.

The signal is measured on a "spot", i.e. a continuous and discreet portion of the sensitive area. It is a portion of the sensitive area where several ligands located in proximity to one another are each bound to a compound and, where appropriate, which is separated from one or more other similar portions of the sensitive area. The spot is so called in reference to the ELISPOT technique, and corresponds to a portion of the sensitive area in contact with the secretions of an individual cell. A portion is said to be continuous when it does not comprise several distinct subportions emitting a signal, separated by subportions not emitting a signal; in other words, the whole of the continuous portion emits a signal. A portion is said to be discreet when it has a limited surface area, related to the maximum distance of diffusion of the secretions originating from a cell during the culture. Consequently, the measurement of the signal emitted by a spot, i.e. a continuous and discreet portion, of the sensitive area aims to make sure that the secretions originating from an individual cell are indeed measured.

A culture chamber according to the invention can comprise one or more sensitive areas, it being possible for each sensitive area to be specific for a single compound or for different compounds. As will be clearly apparent to those skilled in the art, the specificity of each sensitive area with respect to one or more compounds is borne by the ligand(s) of which it is composed. Thus, each sensitive area according to the invention can comprise a plurality of identical or different ligands which bind specifically to one and the same compound, or several groups of ligands respectively specific for several different compounds.

Moreover, it can be envisioned that the method according to the invention uses, in addition to a sensitive zone, an area of the solid support not comprising a ligand or comprising a ligand not specific for the compound, in order to be able to measure the signals originating from a nonspecific interaction of the compound with the solid support or with a ligand.

The method of the invention makes it possible to measure the secretions originating from an individual cell, in other words a single cell, i.e. the secretions originating from a lone cell can be measured and distinguished from the secretions of cells that would also be present in the culture chamber, whether these cells are of the same cell type, in the case of a homogeneous population of cells, or of different cell types, in the case of a heterogeneous population of cells.

As will be clearly apparent to those skilled in the art, the individual cell according to the invention may be of any phylogenetic or histological origin. In particular, the individual cell according to the invention may originate from cells which are isolated cells in their natural environment or else from cells which are associated with other cells, whether by direct physical interactions, which may or may not be transient, or by remote interactions, in particular via the emission and reception of biochemical messengers.

Thus, preferably, the cell according to the invention is selected from the group consisting of bacterial cells, fungal cells, algal cells, protozoan cells, and metazoan cells, such as cells of a plant or an animal. Moreover, various types of cells may be present in the culture chamber.

Also preferably, the cell according to the invention originates from a biological sample, from a food sample, from a water sample, in particular fresh water, seawater or wastewater sample, from a soil sample, from a sludge sample or from an air sample. More preferably, the cell according to the invention originates from a biological sample, such as:
blood,
cerebrospinal fluid, an oral secretion, in particular saliva,
sperm,
a vaginal secretion,
urine,
feces,
synovial fluid,
a biopsy,
a specimen originating from a lavage of an organ or of an anatomical cavity, in particular a lavage of the nose, mouth, throat, stomach, intestines or vagina, or a bronchoalveolar lavage of the lungs,
a sample from drainage of a biological fluid, in particular ascites fluid, lymphatic fluid, pus or bile, or
a cutaneous or conjunctival serous fluid.

It is also preferred for the cell according to the invention to be selected from the group consisting of immune cells, nerve cells, endocrine cells, stem cells, epithelial cells, cells infected with an infectious agent, such as a virus, a bacterium or a protozoan, and cancer cells.

The compound according to the invention may be of any type capable of being secreted by a cell.

Thus, from a structural point of view, this may involve single-molecule compounds or multimolecular compounds resulting from the noncovalent association of a limited number of subunits, generally less than 10 subunits, such as a protein, a polypeptide or a peptide, a lipid, a glycoprotein, a glycolipid, a lipoprotein, an inorganic ion, or a small organic molecule, preferably comprising from 1 to 100 carbon atoms. It may also involve particulate or supramolecular compounds, such as a vesicle, in particular an exosome, or a microbial particle, such as a viral particle for example.

Moreover, from a functional point of view, the compound according to the invention is preferably selected from the group consisting:
of intercellular signaling compounds, such as a hormone, a neurotransmitter, a cytokine or a chemokine,
of an extracellular matrix protein;
of an immunoglobulin;
of an infectious agent, such as a bacterium, a virus or a protozoan parasite, or of a subunit of an infectious agent, i.e. a constituent or production of an infectious agent, such as a viral particle or protein or a bacterial toxin.

The ligand according to the invention is specific for the compound, i.e. it binds specifically or preferentially to the compound when the compound is present in a mixture comprising different molecules. The ligand according to the invention may be of any nature. Thus, it may be a peptide, a polypeptide, a protein, a glycoprotein, an oligosaccharide, a polysaccharide, a nucleic acid, a lipid, a glycolipid, a lipoprotein, a polymer, in particular suitable for the specific attachment of inorganic ions, such as those described by Lange et al. (2008) *Anal. Chim. Acta* 614:1-26, or for the attachment of a sugar, such as glucose, in particular by a polymer of the poly(N-isopropylacrylamide) (pNIPAM) or pNIPAM-co-acrylamidophenylboronate (pNIPAM-co-APBA) type, or an organic compound comprising from 1 to 100 carbon atoms. Preferably, the ligand according to the invention is selected from the group consisting of an antibody, an antibody fragment, in particular comprising the antigen-binding part of the antibody, a scFv, an antigen, a hapten, an aptamer, a lectin and a chelating agent.

The solid support is suitable for measuring the signal. It may be a support made of glass; of silicon; of organic polymer material, in particular of acrylate, polydimethylsiloxane (PDMS), cyclic olefin copolymer (COC), polyether ether ketone (PEEK) or nitrocellulose type; made of a metal material, in particular silver, gold or platinum; of a carbon-based conductor, in particular of glassy carbon, graphite, grapheme, carbon-based nanostructure, or diamond type; or of a combination of at least two of these materials.

When the measurement is carried out by surface plasmon resonance, the solid support is suitable for plasmon excitation and for the propagation of an evanescent wave at its surface. A transparent material, for example glass, coated with a metal layer, especially of gold, in particular with a thickness of 10 to 100 nm, and more particularly a thickness of 50 nm, will then be preferred.

The attachment of the ligand to the solid support in order to form the sensitive area according to the invention can be carried out by any suitable technique. Simple adsorption, electrostatic interactions, or covalent grafting can in particular be envisioned. By way of example, when the solid support is glass, it will be preferred to use reagents of silane type; when the solid support is made of gold or comprises a part made of gold, it will be preferred to complex ligands on the metal by means of a thiol function. It is also possible to immobilize the ligands in polymer matrices.

Preferably, the ligand density in a sensitive area according to the invention is $10^8$ to $10^{12}$ ligands/mm².

The culturing according to the invention is carried out in vitro in a medium which allows the compound to diffuse from the cells to the ligands. In addition, as will be clearly apparent to those skilled in the art, the culturing according to the invention is carried out so as to obtain survival of the cells and to allow secretion of the compound by the cells. Thus, the culturing according to the invention is preferably carried out in a liquid medium or fluid medium, such as a gelled medium. The techniques and the conditions for cell culture, in particular in a liquid medium or a fluid medium, are well known to those skilled in the art, who know in particular how to define, for each microorganism and each cell type, the appropriate nutritive medium, the optimum culture temperature, for example 37° C. for many mammalian cells, and also the atmosphere necessary for maintaining the viability of the cells. The culturing time can also be adapted for each cell type, depending on its secretion rate. Generally, the culturing time will be less than 24 h. In addition, the culturing may be stopped as soon as it has been possible to obtain the desired information, such as the detection of a secreted compound.

As will be clearly understood by those skilled in the art, when the cell according to the invention originates from a sample or from a composition, the culturing according to the invention, of the cell, can be carried out directly from the sample or from the composition, or else after isolation and/or concentration of the cells. Preferably, the culture chamber wall comprising at least one sensitive area according to the invention is a basal wall toward which the cells can sediment. More preferably, the amount of cells in the culture chamber, related to the surface area of the sensitive area, is from 1 to $10^6$ cells/mm².

Besides, it is preferred that the method of the invention involves culturing a suspension of cells, in particular an homogenous suspension of cells, i.e. a suspension where all cells are of the same type, the concentration of which is below 200 000 cells per milliliter, and more preferably the concentration of which is comprised between 1 000 and 50 000 cells per milliliter. By way of example, in the case of a population of cells originating from a same hybridoma which secretes a monoclonal antibody, a suspension of cells comprising from 10 000 to 50 000 cells per milliliter will be cultured.

In the case where the suspension is not homogenous, i.e. it is a complex suspension comprising a plurality of different cell types and/or subtypes, and only a fraction of the cells secretes compounds according to the invention, it is then preferred that the fraction of secreting cells is below 90% of the total number of cells in the suspension. In particular, it is preferred that the fraction of secreting cells represents between 0.0001% and 50% of the total number of cells in the suspension. By way of example, in the case of a non-homogenous cell suspension consisting of splenocytes, it is possible, in accordance with the invention, to measure the secretion of interferon gamma (IFNγ) by at least on individual T lymphocyte, T lymphocytes T representing from 35% to 40% of the of total population of splenocytes of the suspension. In another example, in the case of a non-homogenous cell suspension of T lymphocytes, it possible, in accordance with the invention, to measure the secretion of interleukin 2 (IL2) by at least one individual CD4+T lymphocyte, CD4+T lymphocytes representing about 60% of the total population of T lymphocytes of the suspension.

EXAMPLE

In this example, the interferon gamma (IFNγ) secreted by mouse splenocytes was detected in real time, on the individual-cell scale, by surface plasmon resonance imaging (SPRi), following cell stimulation using concanavalin A (conA). The stimulated cells were studied, as were cells that were not stimulated, and therefore not secreting IFNγ, that were used as a negative control, on the same device.

1. Experimental Device and Reagents

Figure 1:
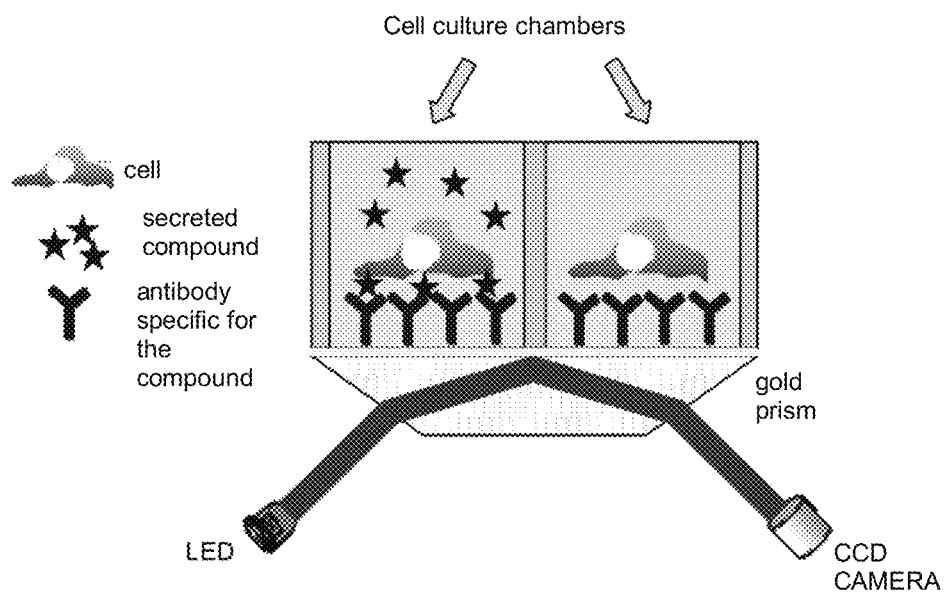
FIG. 1 is a diagrammatic representation of the experimental device used in the example. The sensitive area of the device (gold prism) is chemically modified by the attachment of antibodies specific for a compound secreted by cells. Two cell samples were cultured together on the device: in the culture chamber on the left, cells secreting the compound of interest, and in the culture chamber on the right, cells not secreting this molecule. This configuration comprising two culture chambers makes it possible to measure and quantify the nonspecific parasitic signals. The secreted compound is detected in real time, and without labeling, by SPRi, using a LED, a polarizing filter and a CCD camera.

In this example, the device (see FIG. 1) comprises:
two culture and analysis chambers containing AIMV medium (Gibco) making it possible to maintain in culture (viability and secretory activity) two cell samples in parallel;
a rat monoclonal antibody directed against mouse interferon gamma (anti-IFNγ, BD biosciences) used as specific ligand for the secreted product;
a glass prism coated with a 50 nm film of gold (GenOptics) as solid support for the anti-IFNγ antibody;
an SPRi-lab+ surface plasmon resonance imager (GenOptics) as signal transduction element enabling real-time optical reading of the interactions between the antibody (anti-INFγ IgG) and the secreted compound (mouse INFγ);
an incubator (Memmert) for maintaining the whole of the device at 37° C., a temperature favorable to cell secretion.

Reagents required:
Phosphate buffered saline (PBS, Sigma-Aldrich);
Roswell Park Memorial Institute culture medium (RPMI, Sigma-Aldrich);
11-Mercaptoundecanoic acid (Sigma-Aldrich);
N,N'-Dicyclohexylcarbodiimide (DCC, Sigma-Aldrich);
N-hydroxysuccinimide (NHS, Sigma-Aldrich);
dimethylformamide (DMF, Sigma-Aldrich);
Antibiotic solution: 5000 U/ml penicillin—5 mg/ml streptomycin (Sigma-Aldrich);
Concanavalin A (Sigma-Aldrich).

2. Production of the Sensitive Area: Attachment of the Antibodies to the Gold Surface The antibodies were attached to the gold surface by complexation of thiolated products. Briefly, the antibodies were coupled to a molecule of 11-mercaptoundecanoyl-1-N-hydroxysuccinimide ester (Thiol-NHS), synthesized using 11-mercaptoundecanoic acid, N,N'-dicyclohexylcarbodiimide (DCC) and N-hydroxysuccinimide (NHS) in dimethylformamide (DMF). The coupling with the antibody was carried out in PBS equilibrated at pH8, overnight at 4° C., with a Thiol-NHS/antibody molar ratio of 10:1. The antibodies thus coupled were subsequently purified by ultracentrifugation on a membrane having a cut-off threshold of 30 kDa, then concentrated to 2 μM in PBS containing 10% glycerol. The coupled antibodies were deposited and spread out on the gold surface and thus grafted via sulfur-gold bonding. A nonfunctionalized control area and a sensitive area, functionalized with the antibodies, were delimited on the same chip.

3. Cell Culture

Murine splenocytes were taken from a C57Bl/6 mouse. After removal of the spleen, the cells were dissociated on a sieve grille and suspended in a RPMI medium. After centrifugation for 5 min at 300 g, the cell suspension was incubated for 5 min in the presence of a red blood cell lysis buffer (8.3 g/l of $NH_4Cl$, 0.8 g/l of $NaHCO_3$, 0.04 g/l of EDTA) in order to remove this cell type from the sample. After washing in PBS, the cells were again centrifuged (5 min, 300 g) and suspended at a density of $10^6$ cells/ml in RPMI medium containing 10% of fetal calf serum (FCS) and 1% of antibiotic solution. The cell viability was verified by counting after staining with trypan blue. Just before the experiment, the cells were centrifuged for 5 min at 300 g and resuspended at a density of 200 000 cells/ml in a buffered AIMV medium containing or not containing concanavalin A at 2 µg/ml.

4. Detection of Cell Secretions

Before the analysis, the sensitive area was treated by incubation in AIMV medium for 30 min. The prism was then inserted into the SPR imager, under the culture chambers, in order to complete the device. The whole device was placed in an incubator at 37° C. 500 µl of cell suspension prepared as described above were deposited in each of the culture chambers and incubated for the time of the experiment. Thus, cells stimulated with ConA were cultured in one chamber, while nonstimulated control cells were incubated in the other chamber. The binding of the secreted compounds by the antibodies was detected by SPRi. A 12-bit CCD camera made it possible to quantify the signal consisting of the variations in reflectivity caused by the IFNγ-antibody interaction in the sensitive area. Images of the variations in reflectivity at the surface of the sensitive area were recorded in real time.

Figure 2:
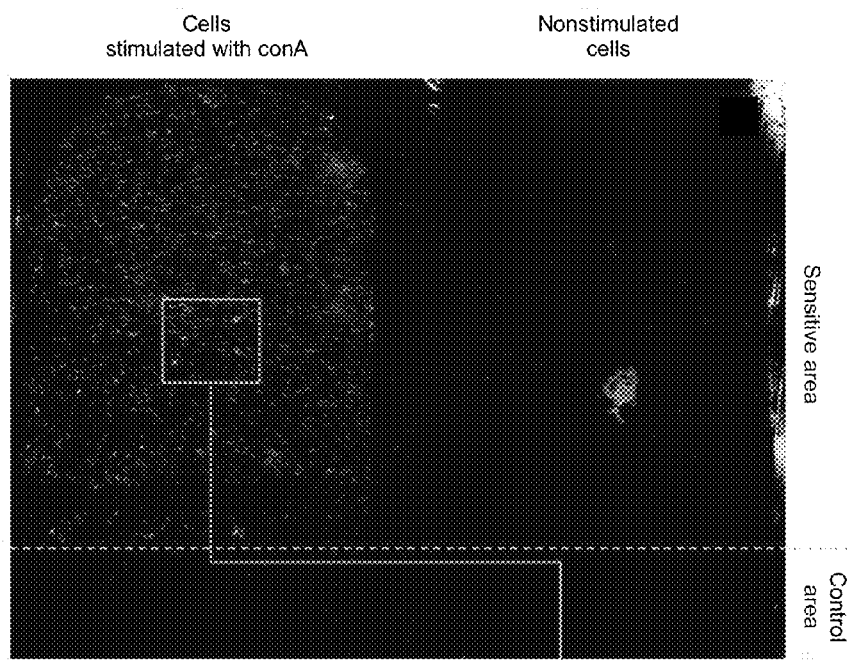
FIG. 2 represents an SPR image of the surface of the gold prism of the device used in the example. This surface is divided up into a sensitive area (at the top) functionalized with the antibody, and a control area (at the bottom) which is not functionalized. The cells were incubated on these areas, in two distinct culture chambers, one in which the cells are not stimulated (on the right), the other in which the cells are stimulated with ConA (on the left). Light spots corresponding to the secreted compounds attached to the sensitive surface appeared on the part of the sensitive area on which the ConA-stimulated cells were incubated (top left). The part of the sensitive area which is boxed-in in white is magnified in FIG. 3.
Figure 3:
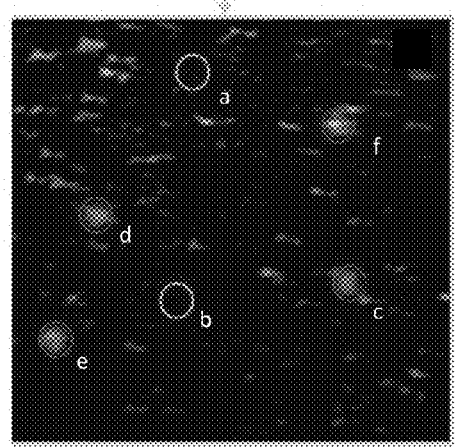
FIG. 3 is a magnification of the part of the sensitive area boxed-in in white in FIG. 2. Masks in the shape of a circle are represented; they delimit portions of interest of the sensitive area corresponding to a spot (circles c, d, e and f). Control portions (no spot) were also selected (circles a and b).

Spots appeared on the surface of the sensitive area (FIG. 2), formed by the compounds secreted by each individual cell that were bound by the antibodies of the sensitive area. "Masks" were then drawn on the images (represented by the circles denoted by a, b, c, d, e, and f in FIG. 3) in order to delimit portions of the sensitive area corresponding, a priori, to antibodies binding the IFNγ produced by one and the same cell (circles c, d, e and f). Portions with no spot were also selected as controls (circles a and b) in the sensitive area in the presence of stimulated cells.

The mean of the variation in reflectivity per pixel contained in each of the portions selected was plotted over time for each portion c, d, e and f (likewise for the control portions a and b). The variation in "relative reflectivity" expressed as percentage reflectivity, of the portions of the sensitive area containing the stimulated cells, was calculated by subtraction of the background noise, i.e. of the mean variation in reflectivity recorded in the part of the sensitive area containing the nonstimulated and therefore nonsecretory control cells (FIG. 4).

Figure 4:
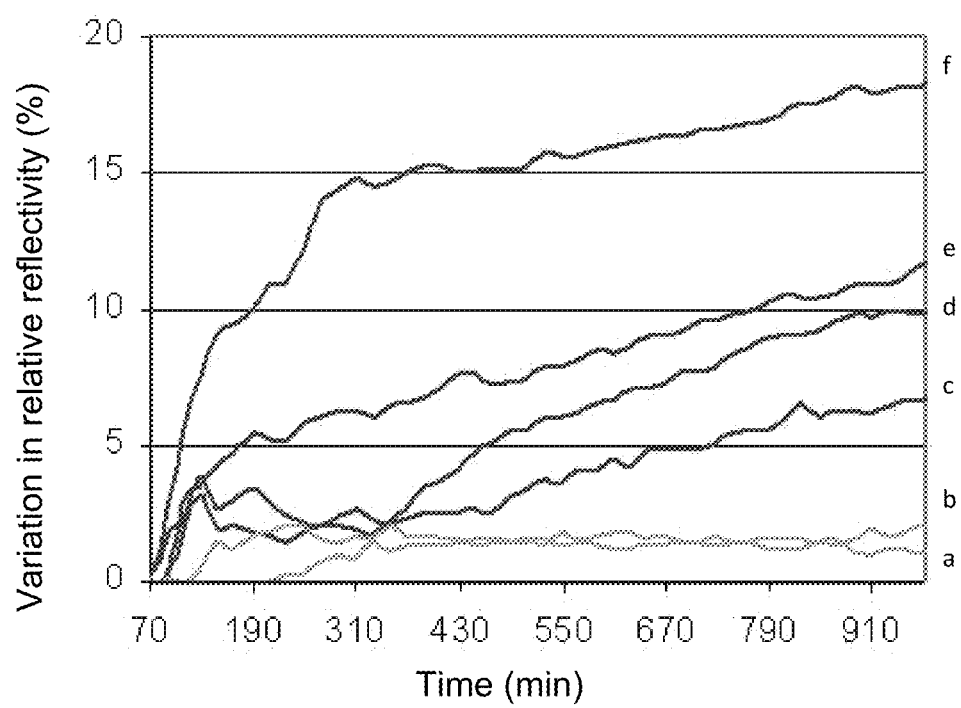
FIG. 4 represents the variation in relative reflectivity (y-axis, as %) of the portions a, b, c, d, e and f of the sensitive area that are represented in FIG. 3, as a function of time (x-axis, in minutes).

The curves c, d, e and f of FIG. 4 show variations in reflectivity with kinetics specific to each spot, thus demonstrating individual behaviors specific to each cell.

What is claimed is:

1. A method for measuring real-time secretion of a compound by an individual cell, the method comprising:
    (a) culturing the cell in a culture chamber comprising a wall with an area sensitive to the secreted compound, wherein the sensitive area comprises: (i) a ligand attached to a solid support and is capable of binding specifically to the compound and (ii) an optical reading system for measuring in real-time a signal produced during, from, or during and from, the binding of the compound to the ligand, wherein the signal is not mediated by molecules added to, or present in, the culture chamber other than the compound and the ligand;
    (b) identifying, in the sensitive area, a spot emitting the signal produced in (a), the spot being defined by a continuous and discrete portion of the sensitive area in contact with the secretions of the individual cell, wherein the whole of the portion emits signal; and
    (c) measuring in real-time the signal produced by the spot, wherein the signal represents the amount of the compound secreted by the individual cell.

2. The method of claim 1, wherein the signal is measured using a near-field optical technique.

3. The method of claim 1, wherein the cell is bacterial, fungal, algal, protozoan, or metazoan.

4. The method of claim 1, wherein the cell originates from a biological sample, a food sample, a water sample, a soil sample, a sludge sample, or an air sample.

5. The method claim 4, wherein the biological sample is blood, cerebrospinal fluid, an oral secretion, sperm, a vaginal secretion, urine, feces, synovial fluid, a biopsy, a specimen originating from a lavage of an organ or of an anatomical cavity, a sample from drainage of a biological fluid, a specimen of a cutaneous or conjunctival serous fluid, or combinations thereof.

6. The method of claim 1, wherein the cell is an immune cell, a nerve cell, an endocrine cell, a stem cell, an epithelial cell, a cell infected with an infectious agent, or a cancer cell.

7. The method of claim 1, wherein the compound is a protein, a polypeptide, a peptide, a lipid, a glycoprotein, a glycolipid, a lipoprotein, an inorganic ion, a small organic molecule, a vesicle, a microbial particle, a viral particle, or combinations thereof.

8. The method of claim 1, wherein the compound is an intercellular signaling compound, an extracellular matrix protein, an immunoglobulin, an infectious agent or a subunit of an infectious agent, or combinations thereof.

9. The method of claim 1, wherein the ligand is a peptide, a polypeptide, a protein, a glycoprotein, an oligosaccharide, a polysaccharide, a nucleic acid, a lipid, a polymer, or an organic compound comprising from 1 to 100 carbon atoms.

10. The method of claim 1, wherein the ligand is an antibody, an antibody fragment, a scFv, an antigen, a hapten, an aptamer, a lectin, or a chelating agent.

11. The method of claim 1, wherein the solid support is a material comprising glass, silicon, an organic polymer, a metal material, or a carbon-based conductor.

12. The method of claim 1, wherein the wall of the culture chamber comprising the sensitive area is a basal wall in which cells can sediment, and the amount of cells in the culture chamber is in a range of about 1 to about $10^6$ cells/mm$^2$ of the surface area of the sensitive area.

13. The method of claim 1, wherein the density of the ligand in the sensitive area is in a range of about $10^8$ to $10^{12}$ ligands/mm$^2$.

14. The method of claim 1, wherein the signal is measured by surface plasmon resonance.

15. The method of claim 1, wherein the solid support is glass, silicon, an organic polymer, metal, a carbon based conductor, or combinations thereof.

16. The method of claim 15, wherein the solid support is glass.

17. The method of claim 16, wherein the glass is a glass prism coated with a 50 nm film of gold.

18. The method of claim 1, wherein the ligand is an antibody or an antigen binding fragment thereof, an antigen, a hapten, an aptamer, a lectin, or a chelating agent.

19. The method of claim 18, wherein the antibody is a monoclonal antibody or an antigen binding fragment thereof.

* * * * *